United States Patent [19]

Gugino

[11] Patent Number: Plant 6,286

[45] Date of Patent: Sep. 13, 1988

[54] GERANIUM NAMED 'GUGINO'S NELL'

[76] Inventor: John L. Gugino, 1472 Dial's Mill Rd., Statham, Ga. 30666

[21] Appl. No.: 920,442

[22] Filed: Oct. 20, 1986

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Charles W. Rummler

[57] ABSTRACT

A new geranium cultivar distinguished by its rose-red flowers of medium size borne on a rigid, upright stem and having a continuous and abundant flowering habit throughout the year with adequate greenhouse photoperiod for wintertime blooming. The plant has a vigorous and rapid growth rate with excellent branching off the main leader, an abundant production of foliage, and its blooms have a lasting quality of 10 to 14 days.

1 Drawing Sheet

BACKGROUND OF THE NEW PLANT

My new geranium plant originated as a sport of 'Sybil Holmes' (unpatented), the new plant having been discovered among plants grown from cuttings of 'Sybil Holmes' produced at my nursery at Statham, Ga., in 1984, this sport being noted by the very rose-red coloration of its blooms, which is much deeper than that of 'Sybil Holmes', and the discovery plant was propagated by me by means of cuttings at my greenhouse in Statham. Further propagation by cuttings from successive generations of the new plant at my greenhouse in Statham has shown that its distinctive and novel characteristics hold true from generation to generation and appear to be firmly fixed.

DESCRIPTION OF THE DRAWING

My new geranium plant is illustrated by the accompanying full color photographic drawings which, in FIG. 1, show a potted plant in full bloom, and in FIG. 2, show a close-up view of a flower and an opening bud, the colors shown being as nearly true to those specified herein as it is reasonably possible to obtain by conventional commercial photographic procedures.

DESCRIPTION OF THE NEW PLANT

Figure 2:
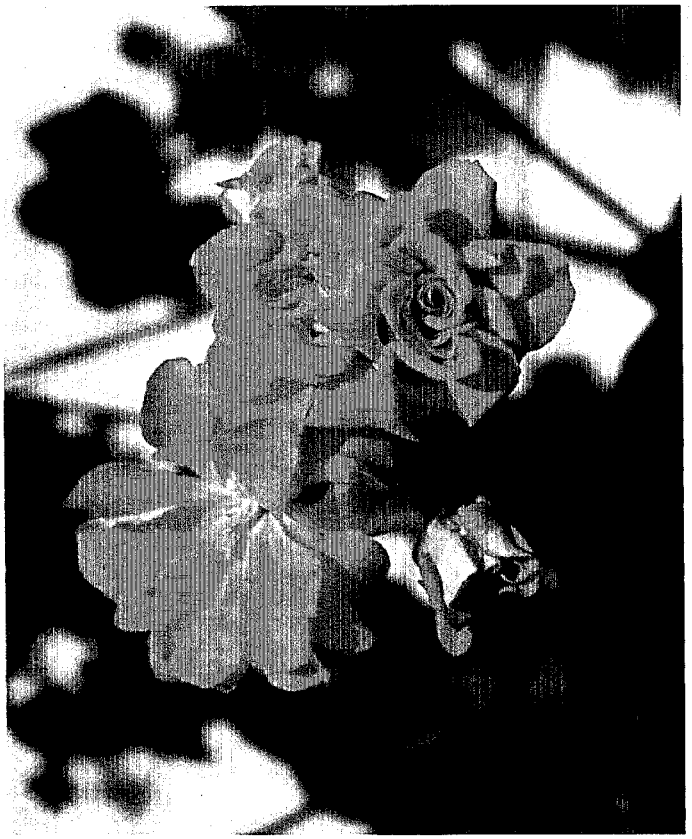
Figure 1:
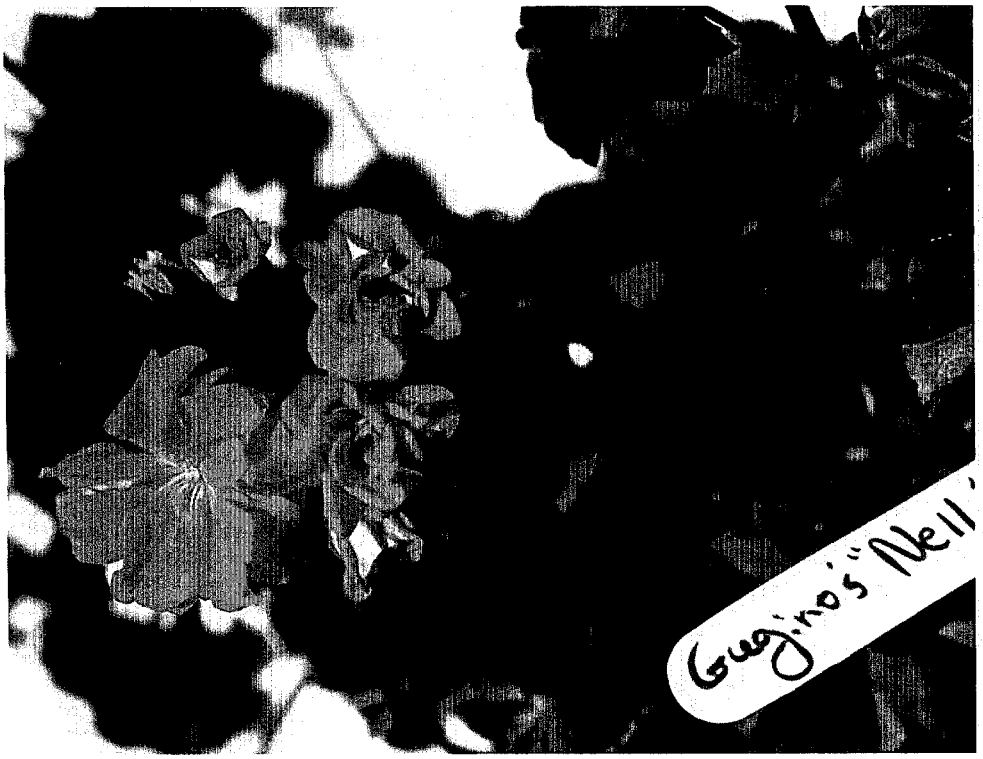

The following is a detailed description of my new geranium cultivar with color designations according to The H.C.C. Colour Chart of The Royal Horticultural Society at London, England, with additional reference to Methuen Handbook of Color by A. Kornerup and J. H. Wanscher, published in 1978 by Hastings House, N. Y., the plant data having been obtained from observations of the plants of this cultivar grown in my greenhouse at Statham, Ga.

THE PLANT

Origin: Sport.
Parentage: 'Sybil Holmes'.
Classification:
- *Botanic.*—*Pelargonium peltatum.*
- *Commercial.*—Geranium cultivar.

Form: Spreading bush.
Height: About 10 inches as a pot plant.
Growth: Vigorous and spreading.
Habit: Free branching and sturdy.
Foliage:

- *Quantity.*—Abundant and heavy.
- *Number of leaves.*—About 7 to 9 per six inches of linear stem growth.
- *Leaf size.*—About 1½ to 2½ inches long and about 1½ to 2½ inches wide.
- *Leaf shape.*—Rounded with lobed and slightly toothed margin.
- *Texture.*—Leathery.
- *Aspect.*—Glossy and smooth.
- *Ribs and veins.*—Five main veins.
- *Color.*—Upper side — Deep green, Methuen 27E8. Under side — Peacock green, Methuen 27D7.
- *Petioles.*—Length: About 1½ to 2½ inches.
- *Stipules.*—Number: Two. Size: About ⅛ to ¼ inch long.

THE BUD

Size:
- *Diameter.*—About ¼ inch.
- *Length.*—About ½ inch.

Shape: Ovoid with acuminate tip.
Rate of opening: Medium.
Color of petals:
- *When sepals first divide.*—Pale red, Methuen 12A3.
- *When petals begin to unfurl.*—Cerise, Methuen 12C8.

Sepals: At first, hooded over the bud.
- *Shape.*—Lanced to ovate.
- *Number.*—About 8 to 12, averaging 10. When the flowers open, the sepals curl back.
- *Color.*—Inside — Peacock green, Methuen 12D7. Outside — Deep green, Methuen 12D8.

Calyx:
- *Shape.*—Pear shaped.
- *Size.*—Long.
- *Aspect.*—Smooth and slightly hairy.
- *Splitting.*—The calyx does split.

Peduncle:
- *Character.*—Rigid.
- *Length.*—About ½ to 1 inch long.
- *Aspect.*—Slightly hairy.
- *Color.*—Peacock green, Methuen 27D7.

THE FLOWER

Blooming habit: Continuous and profuse throughout the year, in greenhouse during winter.
Flower size: Medium.
- *Diameter.*—About 1 inch.

*Depth.*—About ½ to ¾ inch.

Borne: As a cyme.

Shape: Cup shaped when bloom first opens, becoming saucer shaped when bloom matures.

Petalage:

*Number of petals.*—About 25 to 40 per flower, with an average of about 33.

*Arrangement.*—Imbricated.

*Form.*—Obovate with obtuse apex and entire margins.

*Texture.*—Soft.

*Appearance.*—Satiny.

*Color.*—Petal Body, Rose red, HCC 724/1; Methuen 12B8. Base, Rose pink, HCC 427/2; Methuen 12A5. Reverse Side, HCC 427/3; Methuen 12A4. The inside petal colors are essentially the same as the outside petals.

Peduncle:

*Length.*—About 3½ to 4½ inches.

*Character.*—Strong and ascending.

*Color.*—Green.

Discoloration after full bloom: The flowers start with a color of deep cerise and fade to rose pink, HCC 427/2.

Persistence: The florets hang on and dry; but should be beheaded.

Lasting quality: About 10 to 14 days.

REPRODUCTIVE ORGANS

Stamens:

*Number.*—1 to 3.

*Arrangement.*—Random.

*Anthers.*—Size: Average.

*Filaments.*—Length: About 3/16 to 5/16 inch. Color: White.

*Pollen.*—Color: None apparent.

Pistils:

*Number.*—One (five carpels are more-or-less fused into a single pistil).

*Style.*—Length: About ¼ to ¾ inch. Color: Greenish white.

*Stigma.*—Color: Light red.

Character of ovary: Superior, pubescent but appear to be non-functional.

This new geranium cultivar is similar in growth habit and cultural requirements to the cultivar 'Sybil Holmes' but is distinguished by having a deeper flower color and better persistence of bloom. Additionally, the flower of this new cultivar starts out with a deep cerise and fades to rose-pink, thus maintaining a better flower color throughout the entire life of the bloom than 'Sybil Holmes'.

I claim:

1. A new and distinctive geranium cultivar, substantially as herein shown and described, particularly characterized by the rose-red coloration of its blooms, a continuous and abundant year around flowering ability, and by its vigorous and much branched growth habit.

* * * * *